United States Patent
Baer et al.

(10) Patent No.: US 6,495,195 B2
(45) Date of Patent: Dec. 17, 2002

(54) BROADBAND ABSORBING FILM FOR LASER CAPTURE MICRODISSECTION

(75) Inventors: Thomas M. Baer, Mountain View; David F. Head, Los Gatos; John S. Toeppen, Livermore, all of CA (US)

(73) Assignee: Arcturus Engineering, Inc., Mountain View, CA (US)

(*) Notice: Subject to any disclaimer, the term of this patent is extended or adjusted under 35 U.S.C. 154(b) by 0 days.

(21) Appl. No.: 08/800,882

(22) Filed: Feb. 14, 1997

(65) Prior Publication Data

US 2001/0003009 A1 Jun. 7, 2001

(51) Int. Cl.[7] .......................... A61L 31/08; A61B 19/00; B05D 3/06
(52) U.S. Cl. ..................... 427/2.11; 427/2.31; 427/555; 427/556; 427/596
(58) Field of Search ................................. 428/457, 458, 428/460, 461, 480, 328; 422/61; 427/2.11, 2.31, 555, 554, 556, 596; 216/91

(56) References Cited

U.S. PATENT DOCUMENTS

| | | | |
|---|---|---|---|
| 2,801,568 A | 8/1957 | Dakin | |
| 3,680,947 A | 8/1972 | Wanesky | |
| 3,684,099 A | 8/1972 | Kiebach | |
| 3,705,769 A | 12/1972 | Johannsmeier | |
| 3,836,231 A | 9/1974 | Cole, Jr. | |
| 3,848,962 A | 11/1974 | Nelson | |
| 3,853,591 A * | 12/1974 | Haskell | 117/47 A |
| 3,939,019 A | 2/1976 | Pickett | |
| 3,995,941 A | 12/1976 | Nagahara et al. | |
| 4,064,205 A * | 12/1977 | Landsman | |
| 4,080,476 A | 3/1978 | Laskey | |
| 4,149,803 A | 4/1979 | Litz | |
| 4,205,059 A | 5/1980 | von Hagans | |
| 4,210,384 A | 7/1980 | Meyer et al. | |
| 4,245,003 A * | 1/1981 | Oranesky et al. | 427/146 |
| 4,302,480 A | 11/1981 | Fischer et al. | |
| 4,303,866 A | 12/1981 | Porro et al. | |
| 4,320,157 A | 3/1982 | Von Hagens | |
| 4,333,983 A | 6/1982 | Allen | |
| 4,436,385 A | 3/1984 | Fischer et al. | |
| 4,467,915 A * | 8/1984 | Snyder et al. | 206/219 |
| 4,497,792 A | 2/1985 | Gindler | |
| 4,508,435 A | 4/1985 | Graham et al. | |
| 4,509,834 A | 4/1985 | Hodgson | |
| 4,538,885 A | 9/1985 | Graham et al. | |
| 4,552,033 A | 11/1985 | Marzhauser | |
| 4,559,266 A * | 12/1985 | Misasa et al. | 428/341 |
| 4,588,579 A | 5/1986 | Bachhuber et al. | |
| 4,588,674 A * | 5/1986 | Stewart et al. | 430/273 |
| 4,600,282 A | 7/1986 | Yamamura et al. | |
| 4,614,431 A | 9/1986 | Komeyama | |
| 4,624,915 A | 11/1986 | Schindler et al. | |

(List continued on next page.)

FOREIGN PATENT DOCUMENTS

| | | |
|---|---|---|
| CH | 566 015 A | 8/1975 |
| DE | 19 38 943 | 2/1971 |
| DE | 196 03 996 A1 | 8/1997 |

(List continued on next page.)

OTHER PUBLICATIONS

Dictionary Excerpts: *Hawley's Condensed Chemical Dictionary*, 12th ed; p. 477–479, 501, & 1215, Oct. 18, 1995 *Hackh's Chemical Dictionary*, 4th ed; p. 250, 254 & 712, Sep. 13, 1977.*

(List continued on next page.)

*Primary Examiner*—Marianne Padgett
(74) *Attorney, Agent, or Firm*—Morrison & Foerster LLP (57) ABSTRACT

A thermoplastic film for LCM tissue transfer is thermally coupled to a broadband energy-absorbing material. The broadband energy-absorbing material may either be introduced into the film composition as a dopant or may be in thermal contact with the film.

25 Claims, 4 Drawing Sheets

U.S. PATENT DOCUMENTS

| | | |
|---|---|---|
| 4,627,009 A | 12/1986 | Holmes et al. |
| 4,629,687 A | 12/1986 | Schindler et al. |
| 4,673,261 A | 6/1987 | Hunt et al. |
| 4,684,781 A * | 8/1987 | Frish et al. ................. 219/121 |
| 4,702,565 A | 10/1987 | Schilling et al. |
| 4,731,530 A | 3/1988 | Mikan |
| 4,743,463 A * | 5/1988 | Ronn et al. |
| 4,752,455 A * | 6/1988 | Mayer |
| 4,756,922 A | 7/1988 | Motoyama et al. |
| 4,784,873 A | 11/1988 | Kienecker et al. |
| 4,807,984 A | 2/1989 | Kurimura et al. |
| 4,824,229 A | 4/1989 | Narita et al. |
| 4,836,194 A | 6/1989 | Malluche et al. |
| 4,836,667 A | 6/1989 | Ozeki |
| 4,852,985 A | 8/1989 | Fujihara et al. |
| 4,856,873 A | 8/1989 | Kleinberg |
| 4,871,245 A | 10/1989 | Ishikawa et al. |
| 4,895,735 A * | 1/1990 | Cook |
| 4,901,738 A * | 2/1990 | Brink ........................ 128/849 |
| 4,906,494 A * | 3/1990 | Babinec et al. ........... 428/35.2 |
| 4,911,782 A | 3/1990 | Brown |
| 4,920,053 A | 4/1990 | Inoue et al. |
| 4,923,294 A | 5/1990 | Courtenay |
| 4,954,715 A | 9/1990 | Zöld |
| 4,964,708 A | 10/1990 | Mason |
| 4,987,006 A * | 1/1991 | Williams et al. ............ 427/596 |
| 4,992,660 A | 2/1991 | Kobayashi |
| 5,017,428 A * | 5/1991 | Mecke et al. ............... 428/336 |
| 5,023,187 A | 6/1991 | Koebler et al. |
| 5,029,791 A | 7/1991 | Ceccon et al. |
| 5,057,689 A | 10/1991 | Nomura et al. |
| 5,077,620 A | 12/1991 | Mauro |
| 5,084,356 A * | 1/1992 | Deak ........................ 428/458 |
| 5,089,909 A | 2/1992 | Kleinberg |
| 5,096,775 A * | 3/1992 | Sato et al. ................. 428/327 |
| 5,103,338 A | 4/1992 | Crowlet et al. |
| 5,126,877 A | 6/1992 | Biber |
| 5,132,129 A | 7/1992 | Potter et al. |
| 5,143,552 A | 9/1992 | Moriyama |
| 5,158,895 A | 10/1992 | Ashihara et al. |
| 5,162,941 A | 11/1992 | Favro et al. |
| 5,165,297 A | 11/1992 | Krueger |
| 5,173,802 A | 12/1992 | Heller |
| 5,173,803 A | 12/1992 | Heller |
| 5,192,503 A | 3/1993 | McGrath et al. |
| 5,198,284 A * | 3/1993 | Kitamura .................... 428/195 |
| 5,202,230 A | 4/1993 | Kamentsky |
| 5,217,768 A * | 6/1993 | Walters ..................... 428/35.8 |
| 5,221,698 A | 6/1993 | Amidon et al. |
| 5,225,326 A | 7/1993 | Bresser et al. |
| 5,253,110 A | 10/1993 | Ichihara et al. |
| 5,262,891 A | 11/1993 | Nakasato |
| 5,263,384 A | 11/1993 | Suzuki |
| 5,280,384 A | 1/1994 | Shibasaki |
| 5,288,996 A | 2/1994 | Betzig et al. |
| 5,292,559 A * | 3/1994 | Joyce, Jr. et al. |
| 5,296,291 A * | 3/1994 | Mueller et al. ............. 428/349 |
| 5,296,963 A | 3/1994 | Murakami et al. |
| 5,298,963 A | 3/1994 | Moriya et al. |
| 5,300,540 A | 4/1994 | Masters |
| 5,312,393 A | 5/1994 | Mastel |
| 5,323,009 A | 6/1994 | Harris |
| 5,337,178 A | 8/1994 | Kung et al. |
| 5,345,333 A | 9/1994 | Greenberg |
| 5,346,765 A * | 9/1994 | Maeda et al. ............... 428/354 |
| 5,349,436 A | 9/1994 | Fisch |
| 5,357,366 A | 10/1994 | Marchlenski |
| 5,359,417 A | 10/1994 | Muller et al. |
| 5,367,401 A | 11/1994 | Saulietis |
| 5,378,675 A * | 1/1995 | Takeyama .................. 503/227 |
| 5,386,112 A | 1/1995 | Dixon |
| 5,391,329 A * | 2/1995 | Dougherty et al. .......... 264/1.7 |
| 5,393,647 A | 2/1995 | Neukermans et al. |
| 5,403,970 A | 4/1995 | Aoki |
| 5,412,503 A | 5/1995 | Nederlof |
| 5,416,131 A | 5/1995 | Wolff et al. |
| 5,420,716 A | 5/1995 | Fukaya |
| 5,434,703 A | 7/1995 | Morizumi |
| 5,450,233 A | 9/1995 | Yamamoto et al. |
| 5,455,420 A | 10/1995 | Ho et al. |
| 5,468,967 A | 11/1995 | Chan et al. |
| 5,471,260 A | 11/1995 | Luce et al. |
| 5,479,252 A | 12/1995 | Worster et al. |
| 5,486,335 A | 1/1996 | Wilding et al. |
| 5,492,837 A | 2/1996 | Naser-Kolahzadeh et al. |
| 5,493,861 A * | 2/1996 | Opower ...................... 427/597 |
| 5,494,646 A | 2/1996 | Seymour |
| 5,504,366 A | 4/1996 | Weiss et al. |
| 5,506,725 A | 4/1996 | Koike et al. |
| 5,510,615 A | 4/1996 | Ho et al. |
| 5,513,768 A | 5/1996 | Smith |
| 5,517,353 A | 5/1996 | Ikoh et al. |
| 5,529,841 A | 6/1996 | Neihof ...................... 428/328 |
| 5,531,997 A | 7/1996 | Cochrum |
| 5,532,128 A | 7/1996 | Eggers et al. |
| 5,532,476 A | 7/1996 | Mikan |
| 5,532,873 A | 7/1996 | Dixon |
| 5,535,052 A | 7/1996 | Jorgens |
| 5,536,941 A | 7/1996 | Swann |
| 5,537,863 A | 7/1996 | Fujiu et al. |
| 5,541,064 A | 7/1996 | Bacus et al. |
| 5,552,928 A | 9/1996 | Furuhashi et al. |
| 5,556,790 A | 9/1996 | Pettit |
| 5,557,456 A | 9/1996 | Garner et al. |
| 5,558,329 A | 9/1996 | Liu |
| 5,559,329 A | 9/1996 | Joseph et al. |
| 5,574,077 A | 11/1996 | Dougherty et al. ......... 523/137 |
| 5,576,264 A * | 11/1996 | Ueno ........................ 503/227 |
| 5,578,832 A | 11/1996 | Trulson et al. |
| 5,580,612 A * | 12/1996 | Hickel et al. ............. 427/430.1 |
| 5,587,748 A | 12/1996 | Luce et al. |
| 5,587,833 A | 12/1996 | Kamentsky |
| 5,598,888 A | 2/1997 | Sullivan et al. |
| 5,602,674 A | 2/1997 | Weissman et al. |
| 5,619,035 A | 4/1997 | Weiss et al. |
| 5,621,207 A | 4/1997 | O'Mara |
| 5,621,619 A | 4/1997 | Seffernick et al. |
| 5,631,734 A | 5/1997 | Stern et al. |
| 5,633,535 A | 5/1997 | Chao et al. |
| 5,638,206 A | 6/1997 | Sumiya et al. |
| 5,639,428 A | 6/1997 | Cottingham |
| 5,641,896 A | 6/1997 | Karrai |
| 5,659,421 A | 8/1997 | Rahmel et al. |
| 5,665,582 A | 9/1997 | Kausch et al. |
| 5,674,328 A * | 10/1997 | Mannava et al. ............ 427/596 |
| 5,686,313 A | 11/1997 | Sitte et al. |
| 5,688,592 A * | 11/1997 | Shibahashi .................. 428/323 |
| 5,707,801 A | 1/1998 | Bresser et al. |
| 5,723,290 A | 3/1998 | Eberwine et al. |
| 5,728,527 A | 3/1998 | Singer et al. |
| 5,751,839 A | 5/1998 | Drocourt et al. |
| 5,756,049 A | 5/1998 | Brayton ..................... 422/61 |
| 5,759,781 A | 6/1998 | Ward et al. |
| 5,763,191 A | 6/1998 | Knoll et al. |
| 5,786,022 A | 7/1998 | Agarwal et al. |
| 5,812,312 A | 9/1998 | Lorincz |
| 5,817,462 A | 10/1998 | Garini et al. |
| 5,843,644 A | 12/1998 | Liotta et al. |
| 5,843,657 A | 12/1998 | Liotta et al. |
| 5,859,699 A * | 1/1999 | Baer et al. ................. 356/246 |
| 5,860,937 A | 1/1999 | Cohen |

| | | | |
|---|---|---|---|
| 5,912,134 A | | 6/1999 | Shartle |
| 5,972,667 A | * | 10/1999 | Conia et al. ............. 435/173.2 |
| 5,985,085 A | * | 11/1999 | Baer et al. .................. 156/285 |
| 5,998,129 A | | 12/1999 | Schütze et al. |
| 6,010,888 A | | 1/2000 | Liotta et al. |
| 6,100,051 A | | 8/2000 | Goldstein et al. |
| 6,157,446 A | * | 12/2000 | Baer et al. .................. 356/244 |
| 6,184,973 B1 | * | 2/2001 | Baer et al. .................... 356/36 |
| 6,204,030 B1 | | 3/2001 | Liotta et al. |
| 6,215,550 B1 | * | 4/2001 | Baer et al. .................... 356/36 |
| 6,251,216 B1 | * | 6/2001 | Bonner et al. ............. 428/346 |
| 6,251,467 B1 | * | 6/2001 | Liotta et al. ............... 427/2.11 |
| 6,251,516 B1 | | 6/2001 | Bonner et al. |
| 6,277,648 B1 | | 8/2001 | Colpan |
| 2001/0031481 A1 | | 10/2001 | Liotta et al. |

FOREIGN PATENT DOCUMENTS

| | | |
|---|---|---|
| DE | 196 03 996 A | 8/1997 |
| EP | 1938943 | 7/1969 |
| EP | 0081976 | 12/1982 |
| EP | 0 081 976 B1 | 6/1983 |
| EP | 0 081 976 A1 | 6/1983 |
| EP | 0 388 168 A2 | 9/1990 |
| EP | 0 409 550 A1 | 1/1991 |
| EP | 96/40435 | 6/1995 |
| EP | 97/13838 | 10/1995 |
| GB | 1 317 803 | 5/1973 |
| WO | WO 91/07683 A1 | 5/1991 |
| WO | WO 94/02646 A1 | 2/1994 |
| WO | WO 95/23960 A1 | 9/1995 |
| WO | WO 95/30919 A1 | 11/1995 |
| WO | WO 96/16517 A1 | 5/1996 |
| WO | WO 96/40435 A1 | 12/1996 |
| WO | WO 97/13838 A1 | 4/1997 |
| WO | WO 97/29354 A1 | 8/1997 |
| WO | WO 98/35215 A1 | 8/1998 |
| WO | WO 98/35216 * | 8/1998 |
| WO | WO 98/36261 A1 | 8/1998 |
| WO | WO 99/00658 A1 | 1/1999 |
| WO | WO 99/09390 A1 | 2/1999 |
| WO | WO 99/17094 A2 | 4/1999 |
| WO | WO 99/19341 A1 | 4/1999 |
| WO | WO 99/39176 A1 | 8/1999 |
| WO | WO 99/45094 A1 | 9/1999 |
| WO | WO 00/05587 A3 | 2/2000 |
| WO | WO 00/06992 A1 | 2/2000 |
| WO | WO 99/05587 A2 | 2/2000 |
| WO | WO 00/34756 A2 | 6/2000 |
| WO | WO 00/34756 A3 | 6/2000 |
| WO | WO 00/34757 A1 | 6/2000 |
| WO | WO 00/49410 A2 | 8/2000 |
| WO | WO 00/49410 A3 | 8/2000 |
| WO | WO 00/66994 A2 | 11/2000 |
| WO | WO 00/68662 A1 | 11/2000 |

OTHER PUBLICATIONS

Laser Capture Microdissction, Michael R. Emmer–Buck et al. Oct. 11, 1996, pp 998–1001.

Robert F. Bonner et al. Laser Capture Microdissection: Molecular Analysis of Tissue, Tech .Sight pp 1481–2, Science vol. 287 Nov. 21, 1997.

U.S. patent application Ser. No. 08/984,979, Baer et al., filed Dec. 4, 1997.

U.S. patent application Ser. No. 09/058,711, Baer et al., filed Apr. 10, 1998.

U.S. patent application Ser. No. 09/121,677, Baer et al., filed Jul. 23, 1998.

U.S. patent application Ser. No. 09/121,691, Baer et al., filed Jul. 23, 1998.

U.S. patent application Ser. No. 09/208,604, Baer et al., filed Jun. 25, 1999.

U.S. patent application Ser. No. 09/357,423, Baer., filed Jul. 20, 1999.

U.S. patent application Ser. No. 09/538,862, Baer et al., filed Mar. 29, 2000.

U.S. patent application Ser. No. 09/617,742, Baer et al., filed Jul. 17, 2000.

U.S. patent application Ser. No. 09/706,332, Baer et al., filed Nov. 3, 2000.

Allred, C. D. and Mohsin, S. K. (2000). "Biological Features of Human Premalignant Breast Disease," Chapter 24 *In Disease of the Breast*, 2nd Edition, J. R. Harris, ed., Lippicott Williams & Wilkins: Philadelphia, pp. 355–366. no month.

Bentley–Lawrence, J. et al., (1988). "Sensitive, High–Resolution Chromatin and Chromosome Mapping In Situ: Presence and Orientation of Two Closely Integrated Copies of EBV in a Lymphoma Line," *Cell* 52:51–61. Jan.

Brignole, E. (2000). "Laser–Capture Microdissection," pp. 1–4, located at<<http://pubs.acs.org/subscribe/journals/mdd/v03/i09/html/toolbox.html>> from *Modern Drug Discovery* 3(9):60–70. Nov/Dec.

Chu, S. S. et al. (Apr. 2000). "Laser Capture Microdissection: Applications in Cancer Research," *Biomedical Products* 2514p58:1–3.

Chui, G. (1999). "The Ecosystems Within" *San Jose Mercury News*, Section F, Science & Technology, pp. 1–5. Jun. 22, 1999.

Goldsworthy, S. M. et al. (1999), "Effects of Fixation on RNA Extraction and Amplification from Laser Capture Microdissected Tissue," *Molecular Carcinogenesis* 25:86–91. No month.

Harlow and Lane, eds. (1988). *Antibodies: A Laboratory Manual* Cold Spring Harbor Press: New York, NY, pp. iii–ix (Table of Contents Only). No month.

Heng, H.H.Q. et al. (1992). "High–Resolution Mapping of Mammalian Genes by In Situ Hybridization to Free Chromatin," *Proc. Natl. Acad. Sci. USA* 89:9509–9513. Oct.

Kuska, B. (Dec. 4, 1996). "New Aim–and–Shoot Technique Speeds up Cell Analysis," *J. Natl. Cancer Inst.* 88(23):1708–1709.

Lewis, R. (1998). "Laser Aids Alzheimer's Study," *Biophotonics International* Nov./Dec.:40–41.

Lichter, P. et al. (1990). "High–Resolution Mapping of Human Chromosome 11 by In Situ Hybridization with Cosmid Clones," *Science* 247:64–69. Jan.

Manuelidis, L. et al. (1982). "High–Resolution Mapping of Satellite DNA Using Biotin–Labeled DNA Probes," *The J. Cell. Biol.* 95:619–625. Nov.

Relman, D. A. (1999). "The Search for Unrecognized Pathogens," *Science* 284:1308–1310. May.

van den Engh, Ger et al. (1992). "Estimating Genomic Distance from DNA Sequence Location in Cell Nuclei by a Random Walk Model," *Science* 257:1410–1412. Sep.

Anonymous. (Sep. 22, 1995). "Lazer Hazards," Section II, Chapter 6 *In OSHA Technical Manual.* United States Department of Labor Occupational Safety and Health Administration, pp. 6–1–6–40.

Ashkin, A. et al. (Oct. 1989). "Internal Cell Manipulation Using Infrared Laser Traps," *PNAS USA* 86(20):7914–7918.

Berns, M. et al. (Apr. 1998). "Laser Scissors and Tweezers," *Scientific America*, pp. 62–67.

Böhm, M. et al. (Jul. 1997). "Non–Contact Laser Microdissection of Membrane–Mounted Native Tissue," *Amer. J. of Pathol.* 151(1):63–67.

Burgmeister et al. (Mar. 1998). "Genetic Analysis of Single Cells After Laser Microbeam Seperation: Trophoblastic Cells from Cervical Mucus and Fetal Erythroblasts from Maternal Blood," *Laser Microdissection and Laser Pressure Catapulting*.

Cremer, M. et al. (Mar. 25–28, 1998). "Collection of Individual Chromosomes and Nuclear Segments by Laser Microdissection and Laser Pressure Catapulting," *P.A.L.M. Mikrolaser Technologies Workshop*, Abstract (1 page total).

Friend, T. (Tuesday, Aug. 5, 1997). "Getting Up Close to Cancer Genes," *USA Today* Science section:4D.

Fukui, K. et al. (Jun. 1992). "Microdissection of Plant Chromosomes by Argon–Ion Laser Beam," *Theoretical and Applied Genetics* 84:787–791.

Isenberg, G. et al., (May 1976). "Cell Surgery by Laser Micro–Dissection: A Preperative Method," *Microscopy* 107(1):19–24.

Kubo, Y. et al. (Mar. 1, 1995). "Early Detection of Knudson's Two–Hits in Preneoplastic Renal Cells of the Eker Rat Model by the Laser Microdissection Procedure," *Cancer Res.* 55(5):989–990.

Meier–Ruge, W. et al. (1976). "The Laser in the Lowry Technique for Microdissection of Freeze–Dried Tissue Slices," *Histochem. J.* 8:387–401. No month.

Pontén, F. et al. (1997). "Genomic Analysis of Single Cells from Human Basal Cell Cancer Using Laser–Assisted Capture Microscopy," *Mutation Res. Genomics* 382:45–55. after Jun. but no month given.

Schindler, M. (Aug. 1998). "Select, Microdissect, and Eject," *Nature Biotechnol.* 16:719–720.

Schindler, M. et al. (Jul. 1985). "Automated Analysis and Survival Selection of Anchorage–Dependent Cells Under Normal Growth Conditions," *Cytometry* 6:368–374.

Schütze, K. and Lahr, G. (May 1998). "Laser Microdissection and Laser Catapulting: A Key–Technique for Single Cell Based Gene Analysis," *BIOforum Int'l.*:177–180.

Simone, N. L. et al. (Jul. 1998). "Laser–Capture Microdissection: Opening the Microscopic Frontier to Molecular Analysis," *TIG* 14(7):272–276.

Thalhammer, S. et al. (Jan. 1997). "Laser Microdissection of Metaphase Chromosomes and Characterization by Atomic Force Microscopy," *Biomedical Optics* 2(1):115–119.

Veigel, C. et al. (1994). "New Cell Biological Applications of the Laser Microbeam Technique: The Microdissection and Skinning of Muscle Fibers and the Perforation and Fusion of Sarcolemma Vesicles," *Eur. J. of Cell Biol.* 63:140–148. no month.

Geduspan, J. et al. (May 1992). "A Growth–Promoting Influence from the Mesonephros During Limb Outgrowth," *Develop. Biol.* 151:242–250.

Schütze, K. et al. (1997). "Cut out or Poke in–The Key to the World Of Single Genes: Laser Microanipulation as a Valuable Tool on the Look–Out for the Origin of Disease," *Genetic Analysis: Biomolecular Engineering* 14:1–8. accepted Nov. 1996; No month for Publisher.

Schütze, K. and Lahr, G. (May 1998). "Identification of Expressed Genes by Laser–Mediated Manipulation of Single Cells," *Nuture Biotechnol.* 16:737–742.

* cited by examiner

BROADBAND ABSORBING FILM FOR LASER CAPTURE MICRODISSECTION

BACKGROUND OF THE INVENTION

1. Field of the Invention

The present invention relates to laser capture microdissection. More particularly, the present invention relates to broadband absorbing films for use in laser capture microdissection (LCM).

2. The Prior Art

The LCM technique is generally described in the recently published article: Laser Capture Microdissection, *Science*, Volume 274, Number 5289, Issue 8, pp 998–1001, published in 1996, incorporated herein by reference. The purpose of the LCM technique is to provide a simple method for the procurement of selected human cells from a heterogeneous population contained ion a typical histopathology biopsy slide.

A typical tissue biopsy sample consists of a 5 to 10 micron slice of tissue that is placed on a glass microscope slide using techniques well known in the field of pathology. This tissue slice is a cross section of the body organ that is being studied. The tissue consists of a variety of different types of cells. Often a pathologist desires to remove only a small portion of the tissue for further analysis.

LCM employs a thermoplastic transfer film that is placed on top of the tissue sample. This film is manufactured containing organic dyes that are chosen to selectively absorb in the near infrared region of the spectrum overlapping the emission region of common AlGaAs laser diodes. When the film is exposed to the focused laser beam the exposed region is heated by the laser and melts, adhering to the tissue in the region that was exposed. The film is then lifted from the tissue and the selected portion of the tissue is removed with the film.

Thermoplastic transfer films such as a 100 micron thick ethyl vinyl acetate (EVA) film available from Electroseal Corporation of Pompton Lakes, N.J. (type E540) have been used in LCM applications. The film is chosen to have a low melting point of about 90 C.

The thermoplastic EVA films used in LCM techniques have been doped with dyes, such as an infrared napthalocyanine dye, available from Aldrich Chemical Company (dye number 43296-2 or 39317-7). These dyes have a strong absorption in the 800 nm region, a wavelength region that overlaps with laser emitters used to selectively melt the film. The dye is mixed with the melted bulk plastic at an elevated temperature. The dyed plastic is then manufactured into a film using standard film manufacturing techniques. The dye concentration in the plastic is about 0.001 M.

While the films employed in LCM applications have proved satisfactory for the task, they have several drawbacks. The optical absorption of a dye impregnated film is a function of its thickness. This property of the film may be in conflict with a desire to select film thickness for other reasons.

The organic dyes which are used to alter the absorption characteristics of the films may have detrimental photochemistry effects in some cases. This could result in contamination of LCM samples. In addition, the organic dyes employed to date are sensitive to the wavelength of the incident laser light and thus the film must be matched to the laser employed.

It is therefore an object of the invention to provide a film for LCM applications which overcomes the shortcomings of the prior art.

It is another object of the present invention to provide a simple LCM film to be used in an LCM instrument.

Yet another object of the present invention is to provide an LCM film which is very thin and can have very high optical absorption.

A further object of the present invention is to provide an optical quality LCM film which is not sensitive to the wavelength of the incident laser light.

A further object of the present invention is to provide optical quality LCM films of adjustable thickness.

Another object of the present invention is to provide an LCM film whose optical density can be adjusted so that sufficient light is transmitted through the sample to permit the sample to be viewed with back light illumination.

Yet another object of the present invention is to provide an LCM film which does not use an organic dye that might have detrimental photochemistry effects.

Yet another object of the present invention is to provide an LCM film which does not employ an organic dye which does not have to be dissolved into the EVA polymer at high concentrations.

BRIEF DESCRIPTION OF THE INVENTION

A thermoplastic film for LCM tissue transfer is thermally coupled to a broadband energy-absorbing material. The broadband energy-absorbing material may either be introduced into the film composition as a dopant or may be in thermal contact with the film.

According to one embodiment of the present invention, a film for LCM tissue transfer comprises a layer of a transparent support film; a layer of a broadband absorbing film; and a layer of a low temperature thermoplastic; the absorbing film having an overall thickness chosen to absorb a desired fraction of incident laser light.

According to this embodiment of the invention, the film consists of a sandwich of layers containing a transparent support film such as mylar or polyester, a broadband absorbing film such as a metal film of nichrome or titanium, and a low temperature thermoplastic layer such as ethyl vinyl acetate (EVA). The metal film thickness is chosen so as to absorb a desired fraction of incident laser light. A typical film may absorb say 10% to 90% of the incident light. The metal thickness is adjusted to provide this optical density by controlling the length of time of the sputtering deposition process. The metal absorbing layer can be sandwiched between two layers of EVA if desired.

A method for fabricating a multilayer film for LCM tissue transfer comprises the steps of: providing a support layer; forming a thin layer of a broadband absorbing film onto the support layer, the broadband absorbing film having a thickness chosen to absorb a desired fraction of incident laser light; and coating the broadband absorbing film with a layer of thermoplastic.

According to the method of the present invention, one embodiment of the film is fabricated by evaporating a thin layer of metal film onto the polyester support using a deposition technique such as sputtering. The film thickness is chosen so as to absorb a desired fraction of incident laser light, usually between 10% and 95%. The metal thickness is adjusted to provide this optical density by controlling the length of time of the sputtering deposition process. The polyester/metal film is then coated with a thin layer (a few to 100 microns) of EVA thermoplastic using a spin coater to achieve a uniform layer across the surface. The spin coating process can be repeated several times to adjust the thickness of the EVA film.

According to one embodiment of the present invention, a thermoplastic film is doped with a broadband energy-absorbing material. The dopant concentration is adjusted so as to give a suitable absorption, usually between 10% and 95%, for the desired thickness of EVA film.

According to another embodiment of the present invention, a broadband absorbing material is deposited on a substrate such as a cap for a biological analysis vessel. The metal film is deposited onto the bottom of a cap and then the cap is coated with EVA.

DETAILED DESCRIPTION OF A PREFERRED EMBODIMENT

Those of ordinary skill in the art will realize that the following description of the present invention is illustrative only and not in any way limiting. Other embodiments of the invention will readily suggest themselves to such skilled persons.

Reference is made in the following disclosure to ethyl vinyl acetate (EVA) film as the transfer film. Persons of ordinary skill in the art will recognize that other films having desireable properties for use as the transfer film may also be employed for that purpose and the disclosure is not intended to be limited to LCM films employing EVA transfer films.

The present invention comprises an LCM film employing a broadband energy-absorbing material either doped into the layer of transfer film material or as a film in thermal contact with the layer of transfer film material. The broadband absorber should have a relatively broad absorption line throughout the visible region of the spectrum so that the absorber does not effect the color spectrum of the transmitted light that is used to illuminate the sample.

Metal films, such as nichrome or titanium are examples of a broadband absorber that can be deposited on a surface which can be thermally coupled to the transfer film. Thermal coupling to the transfer film may be accomplished by evaporating a thin layer of broadband absorbing film onto a transparent support film such as mylar or polyester.

Figure 1:
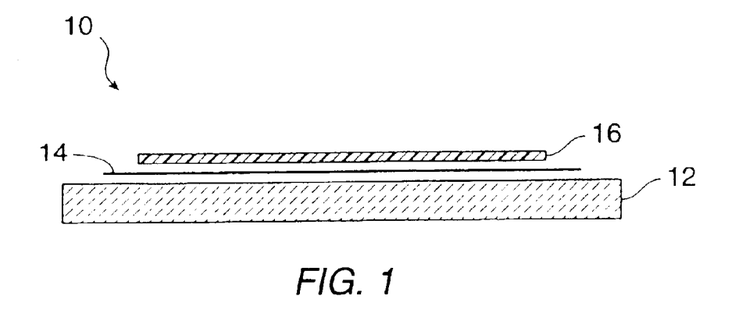
FIG. 1 is a cross sectional view of an LCM tissue transfer film in a multilayer structure according to a first embodiment of the present invention.

Referring first to FIG. 1, a cross sectional view of an LCM tissue transfer film 10 according to a first embodiment of the present invention is presented. The film 10 consists of a sandwich of layers including a transparent support film 12 such as mylar or polyester, a broadband absorbing film 14 such as a metal film of nichrome or titanium, and a low temperature thermoplastic layer 16 such as EVA.

The transparent support layer may have a thickness of between about 25 microns and about 250 microns. The thickness of the broadband absorbing film is chosen so as to absorb a desired fraction of incident laser light. A typical film may absorb from about 10% to about 95% of the incident light. The metal thickness is adjusted to provide this optical density by controlling the length of time of the sputtering deposition process.

The film 10 of FIG. 1 is fabricated by evaporating a thin layer of broadband absorbing film onto the support film using a deposition technique such as sputtering as is known in the art. Another method for depositing metal film coatings is to use electron beam evaporation methods which are well known in the art. The appropriate thickness of the metal film can be determined by monitoring the film deposition process using a witness sample that allows measurement of the optical transmission of the film as a function of deposition time. The deposition is halted when the appropriate transmission level is reached. This is a procedure that is well known to those skilled in the art of thin film coating.

According to a presently preferred embodiment of the invention, the support and broadband absorbing film sandwich is then coated with a thin layer (between a few microns and about 100 microns) of EVA thermoplastic using a spin coater to achieve a uniform layer across the piece. The spin coating process can be repeated several times to adjust the thickness of the EVA transfer film. If necessary, the EVA material may be dissolved in a solvent such as methylene chloride to reduce its viscosity as is well known to those of ordinary skill in the art.

Figure 2:
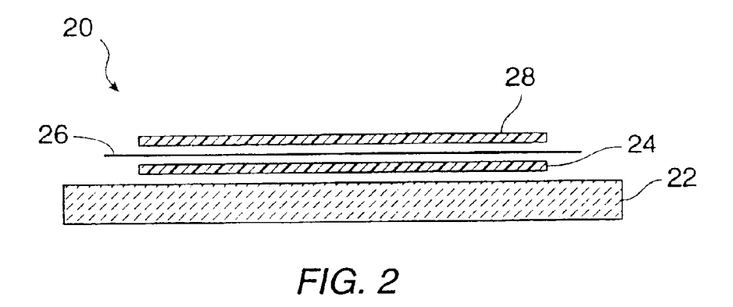
FIG. 2 is a cross sectional view of an LCM tissue transfer film in a multilayer structure according to a second embodiment of the present invention.

Referring now to FIG. 2, a cross sectional view of an LCM tissue transfer film 20 according to a second embodiment of the present invention is presented. The film 20 consists of a sandwich of layers including a transparent support film 22 such as mylar or polyester, a first low temperature thermoplastic layer 24 such as EVA, a broadband absorbing film 26 such as a metal film of nichrome or titanium, and a second low temperature thermoplastic layer 28 such as EVA.

The process for making the film of FIG. 2 is similar to that used to make the film of FIG. 1. The additional EVA layer may be formed by a spin-on process.

In use, the EVA side of the film of either FIG. 1 or 2 is placed in contact with a thin tissue sample. Laser light is focused on the sandwich structure and the light is absorbed by the thin metal film, which raises the temperature of the EVA film and melts the portion of the EVA that is in contact with the region of the metal film that is exposed to the focused laser beam. The laser power is chosen that the temperature rise does not melt the polyester support film. For films contemplated by the present invention, typical laser powers are on the order of 50 mW for film transmissions of about 10%. The melted EVA area adheres to tissue samples which can then be excised by removing the film.

Figure 3:
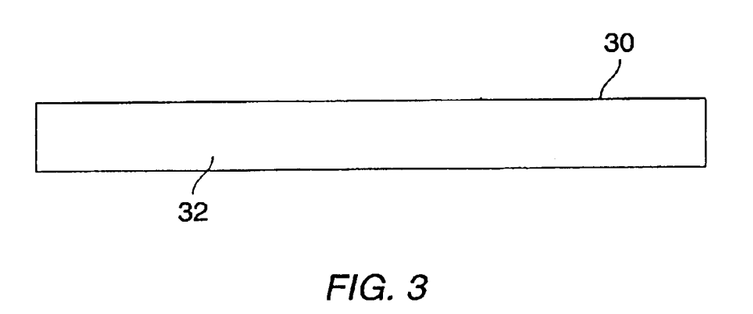
FIG. 3 is a cross sectional view of an LCM tissue transfer film according to a second embodiment of the present invention wherein a broadband energy-absorbing material is doped into the transfer film.

Referring now to FIG. 3, a cross sectional view is presented of an LCM tissue transfer film 30 according to a second embodiment of the present invention wherein a broadband energy-absorbing material is doped into the transfer film. The broadband energy-absorbing material is illustrated as shaded region 32.

An example of a broadband absorber that can be used to dope the EVA plastic is the chemical substance Buckminsterfullerene available as product #379646 from Sigma Chemical Company of St. Louis, Mo. This substance is a pure carbon compound comprising submicron particles that have very broad absorption profiles in the visible region of the spectrum. The Buckminsterfullerene can be mixed with heated EVA and the concentration adjusted so as to give a suitable absorption, usually between 10% and 95%, for the desired thickness of EVA film. The advantage of this method of doping the film is that, unlike the prior art LCM transfer films containing organic dyes, a specific laser wavelength is not required for activation and the extinction coefficient of the Buckminsterfullerene is very high. Moreover, photochemical effects should be reduced compared to those produced using an organic dye.

Figure 4A:
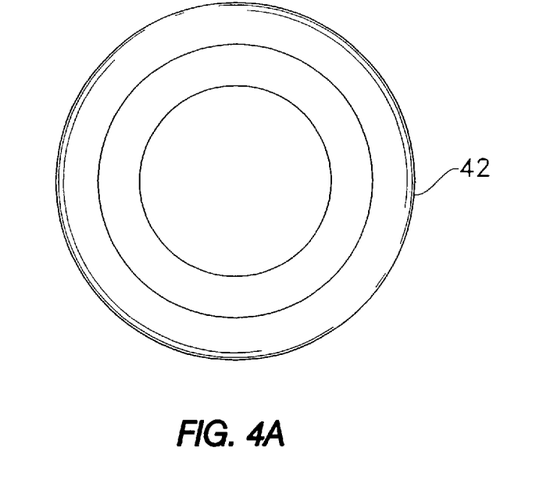
FIGS. 4A, 4B, and 4C show, respectively, bottom view, side view, and side view over a sample vial, of a cap having an LCM tissue transfer film.
Figure 4B:
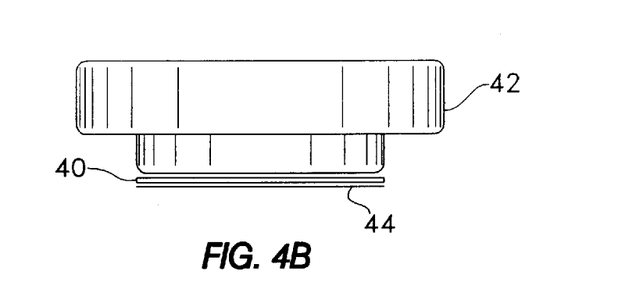
Figure 4C:
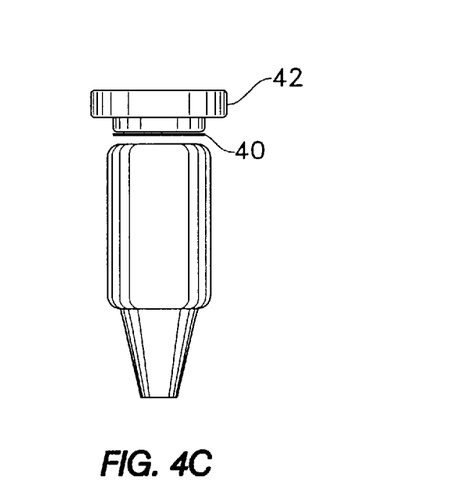

FIGS. 4A, 4B, and 4C show, respectively, a bottom view, A side view, and a side view over a sample vial, of a cap having an LCM tissue transfer film. This variation includes a broadband energy-absorbing material 40 formed on a substrate 42 and a thermoplastic LCM transfer film 44 affixed to the surface of the broadband energy-absorbing material 40. The broadband energy-absorbing material 40 is preferably a metal film such as nichrome or titanium. As may be seen from the Figures, substrate 42 is in the shape of a cap for a biological analysis vessel as disclosed in co-pending application Ser. No. 08/797,026, filed Feb. 7, 1997, now U.S. Pat. No. 5,859,699, issued Jan. 12, 1999, entitled "LASER CAPTURE MICRODISSECTION ANALYSIS VESSEL" expressly incorporated by reference. The biological analysis vessel may be a vessel such as an eppindorf tube or other well-known vessel.

Figure 5:
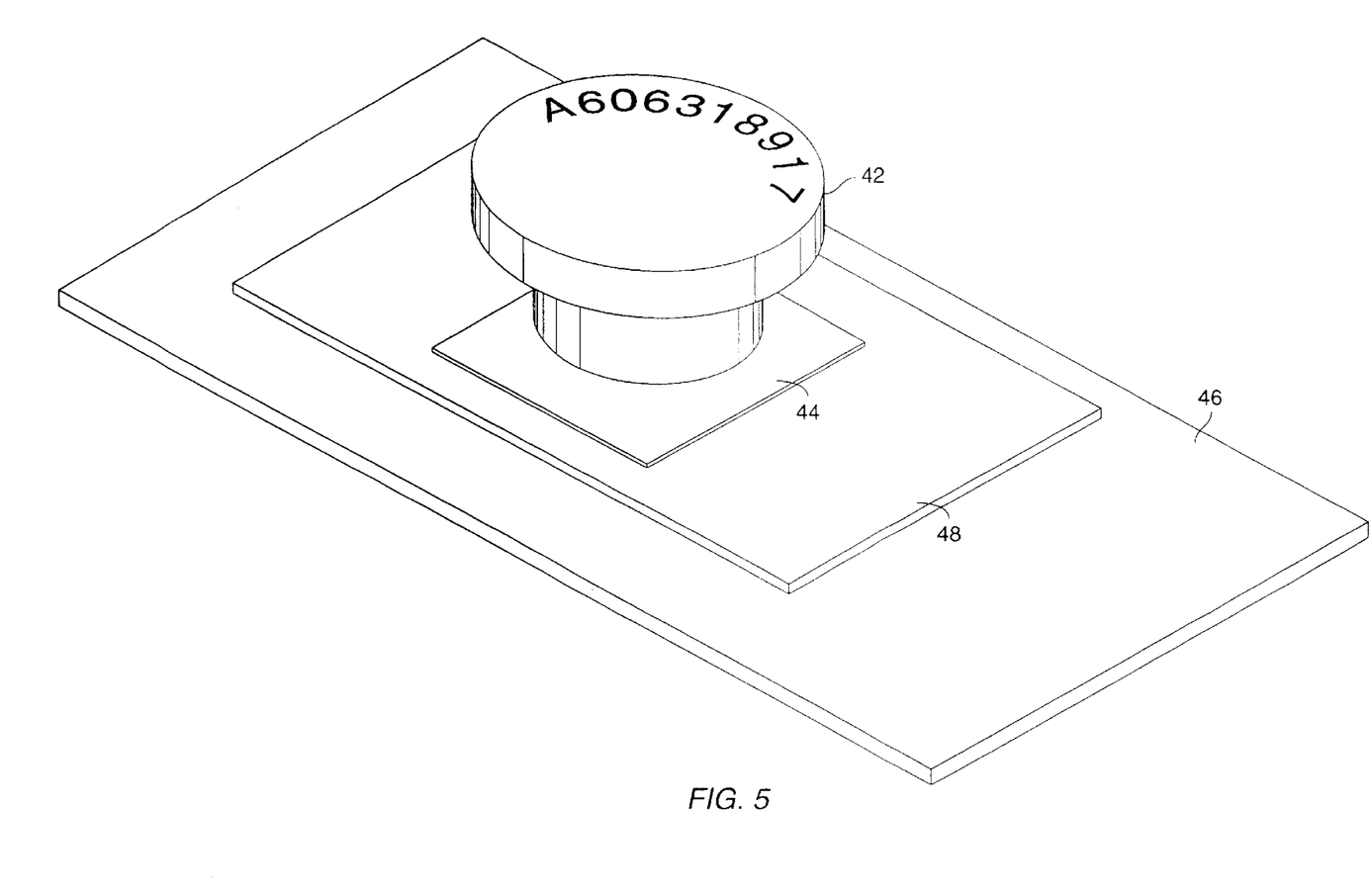
FIG. 5 is a perspective view of a cap for an analysis vessel showing a procedure for affixing the LCM film thereto.

FIG. 5 is a perspective view of a cap 42 for an analysis vessel illustrating a step in a first procedure for affixing the LCM film thereto. Persons of ordinary skill in the art will observe that cap 42 is equipped with a marking means such as a UPC label or laser etched label. Serializing all of the caps provides for easy identification and tracking of cell samples. The label may be read by a sensor, such as a UPC label sensor or OCR sensor which is mounted in or on the laser capture microdissection apparatus.

According to this aspect of the present invention, the serial number is placed on the top of the cap. The serial number is placed on the top of cap 42, and the thickness of cap 42 is selected to be larger than the depth of field of the microscope objective of the LCM apparatus with which cap 42 will be used. Thus, the microscope can be focussed on the tissue sample below the bottom surface of the cap and not have the label or serial number interfere optically, since the label is far from the focal plane of the imaging lens and is thus out of focus.

There are several ways in which the LCM transfer film 44 may be affixed to the surface of the caps according to the present invention. As may be seen from FIG. 5, first, a small, e.g., about 1 cm square piece of thermoplastic film 44 is cut. The film 44 is gently pressed onto the bottom surface of the cap 42 making it stick thereto. A glass microscope slide 46 is heated to about 100 C. on a hot plate. A 0.002 inch thick piece of mylar plastic release liner 48 is placed on the slide. As is known in the art, a release liner is a plastic sheet that is coated with a silicone coating so it does not stick to the thermoplastic film material or the glass slide.

The cap 42 with its attached film 44 is pressed onto the release liner/slide assembly for about 5 seconds or until the film melts. The cap 42 with attached film 44 and release liner 48 is then removed from the hot glass slide 46, cooled down to room temperature, and the release liner 48 is peeled off. Finally, the excess thermoplastic film is trimmed off.

Figure 6:
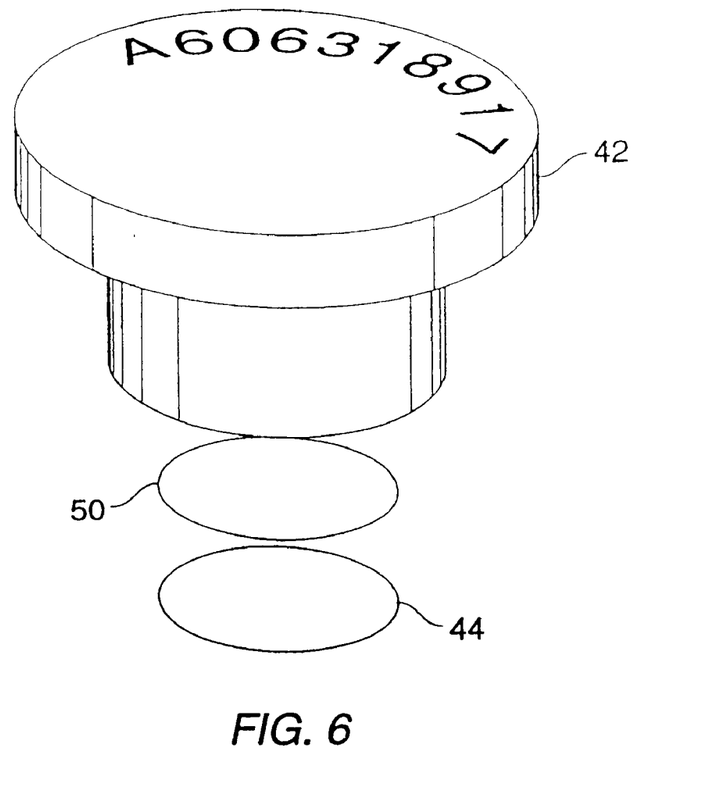
FIG. 6 is a perspective view of a cap for an analysis vessel showing an alternate procedure for affixing the LCM film thereto.

FIG. 6 is a perspective view of a cap for an analysis vessel showing an alternate procedure for affixing the LCM film thereto. According to this method, a piece of transparent double sided adhesive tape 50 (such as standard double stick tape available from 3M Corporation) may be used to tape the thermoplastic film 44 to the bottom of the cap 42. The excess thermoplastic film may then be trimmed off.

There are several advantages inherent in the LCM transfer film of the present invention. The metal film layer can be very thin and still have very high optical absorption. The spin coating process gives optical quality films of adjustable thickness. In addition, the film of the present invention is not sensitive to the wavelength of the incident laser light as are the prior art dye impregnated films.

Another advantage of the present invention is that the broadband energy-absorbing material may be isolated from the tissue sample by the EVA transfer film layer. The broadband energy-absorbing material of the present invention does not use an organic dye that might have detrimental photochemistry effects on the sample with which it is in contact. Also, in embodiments of the present invention which employ a metal film the metal film does not have to be dissolved into the EVA polymer at high concentrations like an organic dye in the prior art films.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A laser capture microdissection method, comprising:
    providing a sample;
    illuminating the sample with light;
    providing a laser capture microdissection transfer film, comprising a thermoplastic film thermally coupled to a broadband energy-absorbing material, said broadband energy-absorbing material having absorption lines throughout the visible region of the spectrum such that said broadband energy-absorbing material does not affect the color spectrum of the transmitted light that is used to illuminate said sample;
    placing said transfer film over said sample;
    focusing a laser beam on a selected region of said sample; laser light of said laser beam being absorbed by said transfer film to activate said transfer film for laser capture microdissection; and
    transferring said sample from said selected region to said transfer film.

2. The laser capture microdissection method of claim 1 wherein said broadband energy-absorbing material is introduced into said thermoplastic film as a dopant.

3. The laser capture microdissection method of claim 1 wherein said broadband energy-absorbing material includes at least one Buckminsterfullerene.

4. The laser capture microdissection method of claim 1 wherein said broadband energy-absorbing material absorbs from about 10% to about 95% of light incident upon said transfer film.

5. The laser capture microdissection method of claim 1 wherein said thermoplastic film includes an ethyl vinyl acetate (EVA) film.

6. The laser capture microdissection method of claim 5 wherein said EVA film has a thickness of about 100 microns.

7. The laser capture microdissection method of claim 1 wherein said broadband energy-absorbing material includes a metal film layer.

8. The laser capture microdissection method of claim 7 wherein said metal film layer comprises a titanium film layer.

9. The laser capture microdissection method of claim 7 wherein said metal film layer comprises a nichrome film layer.

10. The laser capture microdissection method of claim 7 wherein said thermoplastic film comprises ethyl vinyl acetate (EVA).

11. The laser capture microdissection method of claim 10 wherein said broadband energy-absorbing material is introduced into said thermoplastic film as a dopant.

12. The laser capture microdissection method of claim 2 wherein said thermoplastic film comprises ethyl vinyl acetate.

13. A laser capture microdissection method, comprising:
providing a sample;
illuminating the sample with light;
providing a laser capture microdissection transfer film comprising:
  a layer of broadband energy-absorbing film, said broadband energy-absorbing film having absorption lines throughout the visible region of the spectrum such that said broadband energy-absorbing material does not affect the color spectrum of the transmitted light that is used to illuminate said sample; and
  a layer of thermoplastic film,
wherein said laser capture microdissection film has an overall thickness selected to absorb a predetermined fraction of incident laser light;
placing said laser capture microdissection transfer film over said sample;
focusing a laser beam on a selected region of said sample; the incident laser light of said laser beam being absorbed by said transfer film to activate said laser capture microdissection transfer film for laser capture microdissection; and
transferring said sample from said selected region to said transfer film.

14. The laser capture microdissection method of claim 13 wherein said layer of broadband energy-absorbing film comprises a metal film selected from the group consisting of nichrome and titanium, and
wherein said layer of thermoplastic film comprises ethyl vinyl acetate (EVA).

15. The laser capture microdissection method of claim 13 wherein said energy-absorbing film has an overall thickness selected to absorb from about 10% to about 95% of incident laser light.

16. The laser capture microdissection method of claim 13 wherein said layer of support film is transparent.

17. A laser capture microdissection method, comprising:
providing a sample;
illuminating the sample with light;
providing a laser capture microdissection transfer film comprising:
  a first layer of thermoplastic film,
  a layer of broadband energy-absorbing film having absorption lines throughout the visible region of the spectrum such that said broadband energy-absorbing material does not affect the color spectrum of the transmitted light that is used to illuminate said sample, and
  a second layer of thermoplastic film,
  wherein said layer of broadband energy-absorbing film has an overall thickness chosen to absorb a predetermined fraction of incident laser light,
placing said transfer film over said sample;
focusing a laser beam on a selected region of said sample; the incident laser light of said laser beam being absorbed by said transfer film to activate said transfer film for laser capture microdissection; and
transferring said sample from said selected region to said transfer film.

18. The laser capture microdissection method of claim 17 wherein said layer of broadband energy-absorbing film comprises a metal film selected from the group consisting of nichrome and titanium, and
wherein said first and second layers of thermoplastic film comprise ethyl vinyl acetate (EVA).

19. The laser capture microdissection method of claim 17 wherein said broadband energy-absorbing film has an overall thickness chosen to absorb between about 10% and about 95% of incident laser light.

20. The laser capture microdissection method of claim 17 wherein said layer of support film is transparent.

21. A laser capture microdissection method, comprising:
providing a sample;
illuminating the sample with light;
providing a carrier, said carrier comprising:
  a substrate, and
  a laser capture microdissection transfer film mounted on said substrate, said transfer film comprising a thermoplastic film thermally coupled to a broadband energy-absorbing material having absorption lines throughout the visible region of the spectrum such that said broadband energy-absorbing material does not affect the color spectrum of the transmitted light that is used to illuminate said sample;
placing said carrier so that said transfer film is over said sample;
focusing a laser beam on a selected region of said sample; the incident laser light of said laser beam being absorbed by said transfer film to activate said transfer film for laser capture microdissection; and
transferring said sample from said selection region to said transfer film.

22. The laser capture microdissection method of claim 21 wherein said step of providing a carrier further comprises providing a carrier which is transparent at least in a region where said transfer film is mounted thereon.

23. The laser capture microdissection method of claim 21 wherein the step of providing a carrier further comprises providing a carrier wherein said substrate comprises a plastic material.

24. The laser capture microdissection method of claim 21 wherein said substrate is adapted to mate with an analysis vessel.

25. The laser capture microdissection method of claim 21 wherein said substrate is adapted to mate with a holder in a laser capture microdissection sample transfer apparatus.

* * * * *